United States Patent [19]

Yamamoto et al.

[11] Patent Number: 5,294,705
[45] Date of Patent: Mar. 15, 1994

[54] PROCESS FOR THE PREPARATION OF A 3-SUBSTITUTED THIO-3-CEPHEM COMPOUND

[75] Inventors: Yuichi Yamamoto; Tsuneo Okonogi; Seiji Shibahara; Shigeharu Inoue, all of Yokohama, Japan

[73] Assignee: Meiji Seika Kaisha, Ltd., Japan

[21] Appl. No.: 853,730

[22] PCT Filed: Dec. 7, 1990

[86] PCT No.: PCT/JP90/01599
§ 371 Date: Jun. 3, 1992
§ 102(e) Date: Jun. 3, 1992

[87] PCT Pub. No.: WO91/09037
PCT Pub. Date: Jun. 27, 1991

[30] Foreign Application Priority Data

Dec. 7, 1989 [JP] Japan .................................. 1-316424

[51] Int. Cl.$^5$ .............................................. C07D 501/04
[52] U.S. Cl. .................................... 540/226; 540/222; 540/227
[58] Field of Search ............... 540/226, 221, 227, 222

[56] References Cited

U.S. PATENT DOCUMENTS

| 4,812,562 | 3/1989 | Watanabe et al. | 540/226 |
| 4,921,993 | 5/1990 | Yokoo et al. | 540/226 |

FOREIGN PATENT DOCUMENTS

| 2282895 | 3/1976 | France . |
| 2293935 | 7/1976 | France . |
| 62-267228 | 11/1987 | Japan . |
| 1-128986 | 5/1989 | Japan . |

OTHER PUBLICATIONS

Scartazinni et al, Helvetica Chimica ACTA, vol. 58, No. 8, pp. 2437–2450, Dec. 1975.

*Primary Examiner*—Nicholas S. Rizzo
*Attorney, Agent, or Firm*—Larson and Taylor

[57] ABSTRACT

An ester of 7-acylamido-3-acylthio-3- or -2-cephem-4-carboxylic acid represented by general formula (1)

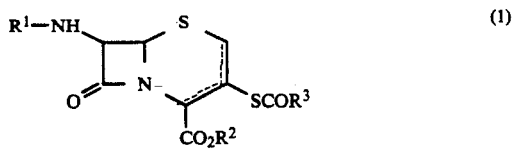

wherein $R^1$ is an acyl group, $R^2$ is a carboxyl-protecting group, $R^3$ is a lower alkyl group, an aryl group or a substituted aryl group, or a mixture of two or more of said ester is used as the starting compound and is reacted wit a tertiary amine and also a secondary amine. Then the tertiary amine salt compound as formed as the reaction product is reacted with a compound of formula (4)

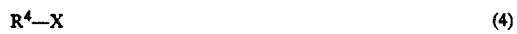

wherein $R^4$ is a lower alkyl group, a cycloalkyl group or a heterocyclic group or a heterocyclic group-substituted methyl group and X is a leaving group, whereby the desired ester of 7-acylamido-3-substituted thio-3-cephem-4-carboxylic acid of formula (5)

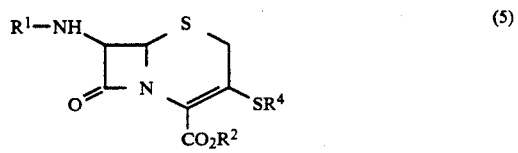

can be produced preferentially, conveniently and efficiently.

4 Claims, No Drawings

PROCESS FOR THE PREPARATION OF A 3-SUBSTITUTED THIO-3-CEPHEM COMPOUND

TECHNICAL FIELD

This invention relates to a process for the preparation of a 3-substituted thio-3-cephem compound. More specifically, this invention relates to a process for the preparation of useful intermediates which may be used for the synthesis of a 3-substituted thio-cephalosporin having a high antibacterial activity and a high absorption capacity in vivo upon oral administration, and this invention also relates to a process for the preparation of protected derivatives of such 3-substituted thiocephalosporin.

BACKGROUND ART

Many investigations have been made in the art for a fairly long time with the intention of producing new cephalosporin compounds having a high antibacterial activity and a high absorption capacity through digestive tracts upon oral administration in combination. Among these compounds, such cephalosporins which are of the type of a 3-substituted thio-3-cephem compound have been considered to be particularly attractive as antibacterial compounds in view of their high absorption capacity through digestive tracts upon oral administration, i.e. excellent absorption in vivo upon oral administration. These 3-substituted thio-3-cephem compounds have been synthesized in the prior art mainly by such method as described in the "Helvetica Chimica Acta", 58, 2437 (1975), wherein the sulfonate or phosphate ester at the 3-enolic hydroxyl group of a 3-hydroxy-3-cephem compound is reacted with a thiol compound in the presence of a base.

However, in the prior art method above-mentioned, the reaction rate of the substitution reaction taking place at the 3-position of the starting cephem compound is not sufficiently high. Thus, in most cases, it was necessary to use the reactant, a thiol compound, and/or a base in excess amount, and occasionally to elevate the reaction temperature in order to proceed with the intended reaction smoothly. The use of such reaction conditions or operations as mentioned above can, sometimes or often, lead to the occurrence of degradation reaction(s) and/or the formation of undesirable secondary product(s), depending upon the natures of side chain at the 7-position and the ester-forming group at the 4-position of the starting cephem compound used. This was one of the major causes for the lowered yield of the 3-substituted thio-3cephem compound formed as the desired final product. In particular, the prior art method usually had a tendency to form the $\Delta^2$ isomer, namely such 2-cephem compound in which the transfer of the double bond in the cephem ring occurred during the reaction, and therefore the $\Delta^2$ isomer, if formed, had to be isomerized into the desired $\Delta^3$ isomer, i.e. the intended 3-cephem compound, by adopting an extra step for achieving such isomerization. A further disadvantage involved in the prior art method above is that some thiol compounds useful as the reactant therein have no good, reasonable method for their synthesis, so that the said prior art method is limited in the range of its application.

DISCLOSURE OF THE INVENTION

We, the present inventors, have proceeded with our investigations with a view to solving the problems discussed above. As a result, we have now developed a new process for the synthesis of a 3-substituted thio-3-cephem compound on the basis of our discovery that the 3-substituted thio-3-cephem compound can be prepared in a high yield and in a simpler way than in the prior art method, by taking particular steps of reacting a 3-acylthio-3- or -2-cephem compound with both of certain tertiary amine and secondary amine, whereby to produce a tertiary amine salt of 3-mercapto-3- or -2-cephem compound having such structure that the tertiary amine is added on the 3-mercapto group of the resulting cephem product, with the reaction being accompanied by cleavage of the acyl group from the 3-thio group of the starting cephem compound, and then subjecting the resulting cephem compound (in the form of the tertiary amine salt obtained) to a substitution reaction for introducing a new substituent into the 3-mercapto group of the said resulting cephem compound.

Thus, according to this invention, there is provided a process for the preparation of a 3-substituted thio-3-cephem compound of general formula (5)

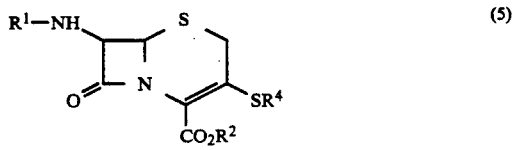

wherein $R^1$ is an acyl group not participating in the reactions intended; $R^2$ is a carboxyl-protecting group; and $R^4$ is a substituted or unsubstituted lower alkyl group, a cycloalkyl group or a heterocyclic group or a heterocyclic group-substituted methyl group, which comprises the steps of reacting a 3-acylthio-cephem compound of general formula (1)

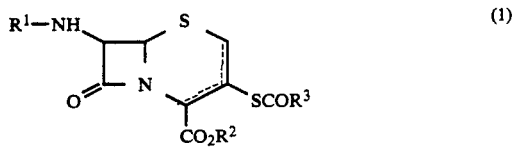

wherein $R^1$ and $R^2$ each have the meanings as defined above; $R^3$ is a substituted or unsubstituted lower alkyl group containing up to 6 carbon atoms, an aryl group or a substituted aryl group; and the dotted line given in the formula (1) represents that the compound of formula (1) is either a compound having a $\Delta^2$ double bond present in the 6-membered ring or a compound having a $\Delta^3$ double bond present in the 6-membered ring or a mixture of the compounds of these two types, with a tertiary amine of formula (2)

wherein $R^5$, $R^6$ and $R^7$ are the same or different and individually represents an alkyl group, particularly a lower alkyl group; or $R^5$ is an alkyl group, particularly a lower alkyl group and $R^6$ and $R^7$ taken together with the nitrogen atom to which $R^6$ and $R^7$ are attached form a nitrogen-containing heterocyclic ring having or not having an oxygen atom as a hetero atom, and also with a secondary amine to give a compound of formula (3)

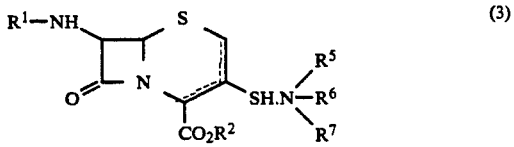

wherein $R^1$, $R^2$, $R^5$, $R^6$ and $R^7$ each have the meanings as defined above; and the dotted line given in the formula (3) also has the meaning as defined above; and then reacting the compound of formula (3) thus formed with a compound of general formula (4)

$$R^4-X \quad (4)$$

wherein $R^4$ has the meaning as defined above; and X is a leaving group, to form the 3-substituted thio-3-cephem compound of general formula (5) above.

BEST MODE FOR WORKING THE INVENTION

In carrying out the process of this invention, the starting compound of general formula (1) is first dissolved in a suitable solvent and is reacted with a tertiary amine of formula (2) and a secondary amine. The acyl group represented by $R^1$ in the starting compound of formula (1) is not particularly limited so long as it does not interfere the reactions involved in the process of this invention. As concrete examples, $R^1$ may be an amino-protecting group of acyl type which is conventionally used in the synthesis of cephalosporins, such as a substituted lower alkanoyl group, particularly a substituted acetyl group. Alternatively, $R^1$ may be an acyl group of such a type which is conventionally used as the side chain on the 7-amino group of antibacterial 3-substituted thio-cephalosporins and which does not participate in the reactions of the process of this invention, for example, phenylacetyl group, phenoxyacetyl group, 2-thienylacetyl group, etc., or an acyl group having a formula (6)

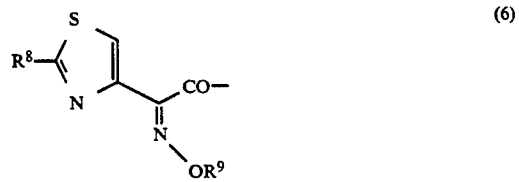

wherein $R^8$ is a protected amino group and $R^9$ is a lower alkyl group containing up to 6 carbon atoms, preferably methyl or ethyl group, and optionally being substituted with a substituted or unsubstituted alkoxycarbonyl group. Namely, the acyl group of formula (6) may be a (Z)-2-(2-substituted aminothiazol-4-yl)-2-substituted or unsubstituted alkoxyiminoacetyl group. The carboxyl-protecting group $R^2$ in the compound of formula (1) may be an esterforming group which protects the 4-carboxyl group and which is removable under mild reaction conditions. As concrete examples of the group $R^2$, there may be mentioned a substituted or unsubstituted lower alkyl group which is conventionally used in the art, such as diphenylmethyl, benzyl, p-methoxybenzyl, p-nitrobenzyl, t-butyl and 2,2,2-trichloroethyl groups etc., or a lower alkenyl group such as allyl group. The group $R^3$ in the compounds of formula (1) may, for example, be a lower alkyl group containing 1 to 6 carbon atoms, preferably a lower alkyl group containing 1 to 4 carbon atoms, such as methyl, ethyl and propyl groups, or an aryl group such as phenyl group, or a substituted aryl group such as p-methoxyphenyl, p-nitrophenyl, p-tolyl, p-chlorophenyl and naphthyl groups, preferably a substituted phenyl group. Preferably, the group $R^3$ is methyl or phenyl group.

In cases where $R^3$ is a substituted or unsubstituted aryl group or a lower alkyl group, such kind of the group $R^3$ is not limited to certain specific aryl or alkyl groups, so long as the acyl group of formula $-COR^3$ attached to the 3-thio group of the compound of formula (1) can be reacted with both the tertiary amine of formula (2) and the secondary amine, preferably a dialkylamine (i.e. a secondary amine) or a nitrogen-containing heterocyclic compound (in the form of a secondary amine) having formula (7)

wherein $R^{10}$ and $R^{11}$ may be the same or different and each are a lower alkyl group, or $R^{10}$ and $R^{11}$ taken with the nitrogen atom to which they are bonded may form a morpholine ring, pyrrolidine ring, piperidine ring or piperazine ring, so that said acyl group $-COR^3$ then can be cleaved by replacement reaction from the compound of formula (1)to form an amide compound of formula (8)

wherein $R^3$, $R^{10}$ and $R^{11}$ have the meanings as defined above, and simultaneously to form a compound of formula (3) in the form of a salt with the tertiary amine used.

However, the acyl group $-COR^3$ may preferably be acetyl group or benzoyl group.

Further, examples of the tertiary amines of formula (2) to be used for the reaction with a compound of formula (1) may include trialkylamines, particularly tri-(lower) alkylamines such as trimethylamine, triethylamine, tributylamine and N,N-diisopropylethylamine; N-(lower) alkyl-morpholines such as N-methylmorpholine; and N-(lower)alkyl-piperidines such as N-ethyl-piperidine. Preferably, the tertiary amine is triethylamine.

Furthermore, the secondary amine to be used for the reaction with a compound of formula (1) may be those of formula (7) as mentioned above, among which morpholine, pyrrolidine, piperidine, piperazine, diethylamine and the like are preferred examples. These tertiary amine and secondary amine each are required to be used in an amount of 1.0 molar equivalent or higher in respect of the compound (1), but each of these amines is most preferred to be used in an amount of 1.0-1.1 molar equivalents to the compound (1).

Solvent suitable for use in the reaction may include a polar organic solvent such as acetonitrile, dimethyl sulfoxide, N,N-dimethylformamide, N,N-dimethylacetamide, N-methylpyrrolidone, hexamethylphosphoric triamide, etc. and other organic solvent such as dichloromethane, tetrahydrofuran, and the like. The reaction temperature is not particularly limited, but ice-cooling or room temperature condition is preferred. The reaction time may vary depending upon the nature of the compound (1) and the reaction conditions employed, but it may usually be within one hour. The completion of the reaction may be confirmed by observing the disappearance of the starting compound of formula (1) used by means of thin layer chromatography and the like. Thereafter, the compound of formula (3) as produced is reacted with a compound of formula (4) which has the substituent R⁴ intended to be introduced onto the 3-thio group of the desired final product of formula (5). At this point, the isolation of the compound of formula (3) from the reaction solution of the preceding step is not always necessary; that is, the compound of formula (4) may be added directly to the reaction solution containing the compound of formula (3) to effect the replacement reaction intended. Some preferred examples of the leaving group X in the compound of formula (4) include a halogen such as chlorine, bromine, iodine, etc. as well as methanesulfonyloxy, para-toluenesulfonyloxy, trifluoromethanesulfonyloxy and alkoxysulfonyloxy groups, etc. Concrete examples of the group R⁴ contained in the compound of formula (4) will be shown hereinafter. The nature of the leaving group X may be chosen to be appropriate by taking into consideration availability or ease of synthesis and reactivity of the compound of formula (4). The compound of formula (4) may be used in an excess amount over 1 mole per mole of the compound of formula (1) as the starting material, and thus in an excess amount higher than 1 mole per mole of the compound of formula (3) formed therefrom, but usually the use of 1.0–5.0 moles of the compound of formula (4) on the same basis is preferred. The reaction medium to be used herein may be the same organic solvent as that used in the preceding reaction. The reaction temperature is not particularly limited, but ice-cooling or room temperature condition is preferred. The reaction time may vary depending upon the reaction conditions to be used, typically the reactivity and amount of the compound of formula (4) and the nature of the solvent used, but is usually within one hour for the completion of reaction.

Concrete examples of the compound of formula (4) may include a dialkyl sulfate where the leaving group X is an alkoxysulfonyloxy group, such as dimethyl sulfate; and further include tetrahydrofurfuryl bromide, α-bromo-γ-butyrolactone, 3-bromotetrahydrofuran, 1-methyl-2-bromomethyl-5-(4-methoxybenzyloxy)-4-pyridone where the leaving group X is bromo group; and others. In general, the group R⁴ of the compound of formula (4) may be an unsubstituted or substituted lower alkyl, cycloalkyl or cycloalkylalkyl groups, of which typical examples are an alkyl group such as methyl and ethyl, cyanomethyl, 2-fluoroethyl, 2,2,2-trifluoroethyl, alkoxycarbonylmethyl, (lower) alkoxyethyl, phenacyl, benzyl, cyclopentyl and cyclopentylmethyl groups. R⁴ may also be a heterocyclic group or a methyl group bearing a heterocyclic substituent, where the heterocyclic group is preferably a saturated or unsaturated heterocyclic group containing one or two (same or different) hetero-atoms selected from O, N and S, the heterocyclic ring being optionally substituted.

Concrete examples of the group R⁴ which represents either a heterocyclic group or a heterocyclic group-substituted methyl group may include the following groups:

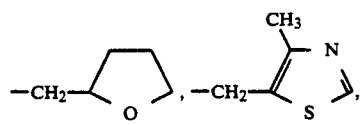

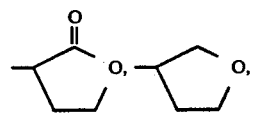

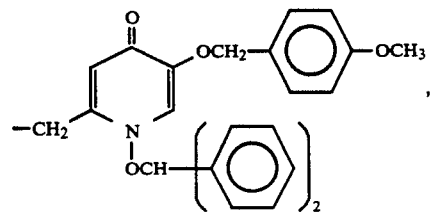

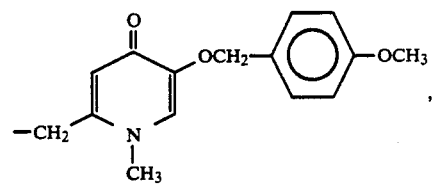

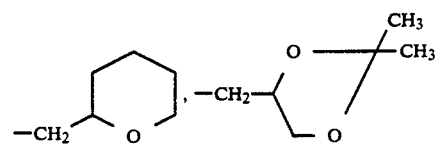

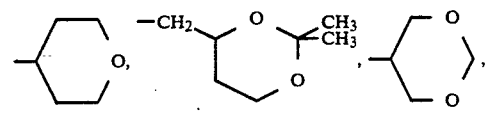

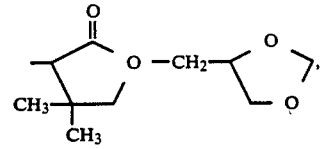

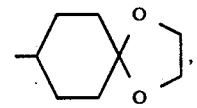

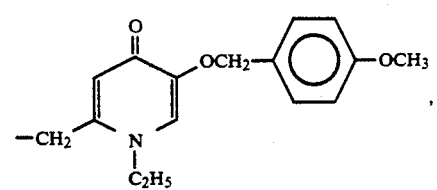

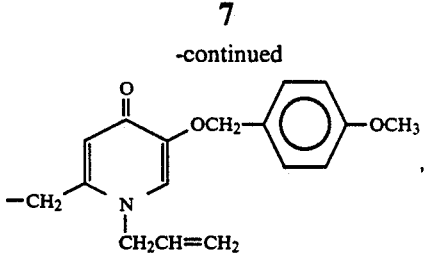

Preferably, the group $R^4$ of the compound of formula (4) is a five- or six-membered heterocyclic group containing one or two oxygen atoms as hetero-atoms, or a methyl group substituted by such a heterocyclic group. As such oxygen-containing heterocyclic group, there may be exemplified tetrahydrofuranyl, tetrahydropyranyl, 1,3-dioxolanyl, 1,3-dioxanyl, 1,4-dioxanyl groups and the like. These heterocyclic groups may be substituted with one or more lower alkyl groups containing up to 4 carbon atoms, where the number and the substituted position(s) on the heterocyclic ring of such substituent(s) are not limited.

In particular, the group $R^4$ is preferably a heterocyclic ring selected from tetrahydrofuranyl group, particularly tetrahydrofuran-2-yl or tetrahydrofuran-3-yl; or tetrahydropyranyl group, particularly tetrahydropyran-2-yl or tetrahydropyran-4-yl; or 1,3-dioxolanyl group; particularly 1,3-dioxolan-4-yl or 2,2-dimethyl-1,3-dioxolan-4-yl; or 1,3-dioxanyl group, particularly 1,3-dioxan-5-yl, 2,2-dioxan-5-yl or 2,2-dimethyl-1,3-dioxan-4-yl. It is also preferable that the group $R^4$ is a methyl group substituted with such heterocyclic group as specifically exemplified above.

The reaction between a compound of formula (3) and a compound of formula (4) results in the formation of a compound of formula (5)

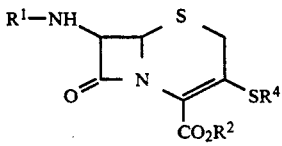

(5)

wherein $R^1$, $R^2$ and $R^4$ have the meanings as defined above, as the replacement reaction product, which is then isolated from the reaction system by after-treatment in a usual manner per se. If necessary, the compound of formula (5) may be purified by recrystallization, reprecipitation or a variety of chromatographic operations.

The process according to this invention has the following great advantages over the prior art methods as above-mentioned.
1. The reaction operation is simple and the yield is high.
2. The amount of the $\Delta^2$ isomer which is prone to be formed as a by-product during the reaction can be significantly lowered by appropriately setting up the reaction conditions.
3. The starting 3-acylthio-cephem compound of formula (1) is preferably in the form of the $\Delta^3$ isomer, but even if the starting compound is in the form of either the $\Delta^2$ isomer or a mixture of the $\Delta^2$ isomer and $\Delta^3$ isomer, the intended 3-substituted thio-3-cephem compound of formula (5), namely the $\Delta^3$ isomer, can preferentially be obtained.
4. Among the compounds of formula (4) useful as the reactant for the reaction with the compounds of formula (3), a dialkyl sulfate and an alkyl halide are more easily available or synthesizable than the corresponding thiols.

In this specification, the expression "a compound having a $\Delta^2$ double bond in the six-membered ring" used for compounds of formula (1) represents that this compound having the $\Delta^2$ double bond is a 3-acylthio-2-cephem compound of the formula:

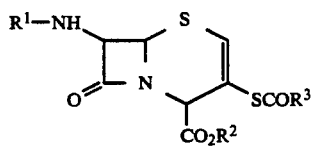

wherein $R^1$, $R^2$ and $R^3$ have the meanings as defined above, and the 2-cephem compound may also be referred to as the $\Delta^2$ isomer. Similarly, the expression "a compound having a $\Delta^3$ double bond in the six-membered ring" used for compounds of formula (1) represents that this compound having the $\Delta^3$ double bond is a 3-acylthio-3-cephem compound of the formula:

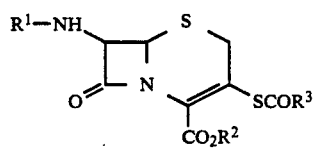

wherein $R^1$, $R^2$ and $R^3$ have the meanings as defined above, and the 3-cephem compound may also be referred to as the $\Delta^3$ isomer. The dotted line given in the formula (1) is to show generically both or either of the $\Delta^2$ isomer and $\Delta^3$ isomer of the cephalosporins, as described in a literature "Cephalosporins and Penicillins, Chemistry and Biology", pages 147–151, edited by Edwin H. Flynn and published by Academic Press, New York and London in 1972.

The compounds of formula (5) which are obtained by the process of this invention are useful as intermediate compounds for the synthesis of not only a variety of known 3-substituted thio-cephalosporins utilizable as antibacterial agents for oral administration, but also such new 3-substituted thio-cephalosporins as proposed recently in the copending Japanese Patent Application No. 316423/89 by the same applicants as in this application (the title of the invention: Cephalosporin derivatives) which are expected to be useful as antibacterial agents for oral administration, and further the compound of formula (5) are also useful as protected derivatives of said new 3-substituted thio-cephalosporins.

The process of this invention is now further illustrated with reference to the following Examples and Reference Examples. It is to be noted that this invention is in no way limited to these Examples and that the process according to this invention is applicable to whatever cases where the starting compound used has substituents $R^1$, $R^2$ and $R^3$ as specified in the general formula (1) even though these substituents are not exemplified in the undermentioned Examples. In Examples given below, all the NMR data show values of chemical shift ($\delta$/ppm) observed at 90 MHz, using TMS as an internal standard.

EXAMPLES 1 p-Nitrobenzyl 7-phenylacetamido-3-acetylthio-3-cephem-4-carboxylate [corresponding to a compound of formula (1)] (265 mg) was dissolved in N,N-dimethylformamide (3 ml) and the resulting solution was cooled to 5° C. To the cooled solution was slowly added a 0.5 ml-portion of a mixture which had been obtained by diluting triethylamine (1.39 ml) used as the tertiary amine and morpholine (0.84 ml) used as the secondary amine in benzene to give 10 ml of said mixture. And, the resulting reaction mixture was stirred at 5° C. for 10 minutes, to form an adduct of p-nitrobenzyl 7-phenylacetamido-3-mercapto-3-cephem-4-carboxylate with triethylamine [corresponding to a compound of formula (3)]. To the resulting reaction solution containing the said adduct was added dimethyl sulfate (72 μl) [corresponding to a compound of formula (4)] and the resulting mixture was stirred for further 10 minutes to effect the reaction. The reaction solution so obtained was diluted with ethyl acetate (8 ml) and diisopropyl ether (8 ml), after which water (8 ml) and 1N HCl (0.5 ml) were added to the diluted solution and the resulting mixture was stirred well. Crystals so formed were recovered from said mixture by filtration, washed with water and with a mixture of ethyl acetate and diisopropyl ether (1 : 1 by volume), successively and dried to afford p-nitrobenzyl 7-phenylacetamido-3-methylthio-3-cephem-4-carboxylate [corresponding to a compound of formula (5)] as pale yellow crystals. Yield: 185 mg (73%).

NMR(CDCl$_3$-DMSO-d$_6$)
2.33(3H, s),
3.56(2H, s),
3.60(2H, s),
4.95(1H, d, J=5Hz),
5.20, 5.38(2H, ABq, J=12Hz),
5.63(1H, dd, J=5Hz, 8Hz),
7.26(5H, s),
7.52(2H, d, J=9Hz),
7.72(1H, d, J=8Hz),
8.13(2H, d, J=9Hz)

EXAMPLE 2

P-Nitrobenzyl 7-phenylacetamido-3-acetylthio-3-cephem-4-carboxylate (132 mg) was dissolved in N,N-dimethylformamide (1.5 ml) and the solution obtained was cooled to 5° C. To the cooled solution was slowly added a 0.25 ml-portion of such a mixture of triethylamine (1.39 ml) used as the tertiary amine and pyrrolidine (0.84 ml) used as the secondary amine which had been diluted in benzene to give 10 ml of said mixture. The resulting reaction mixture was stirred at that temperature for 10 minutes, to form a triethylamine salt of p-nitrobenzyl 7-phenylacetamido-3-mercapto-3-cephem-4-carboxylate in the reaction solution. Then, dimethyl sulfate (36 μl) as methylating agent was added to the reaction solution and the mixture obtained was further stirred for 10 minutes to proceed with the reaction. The resulting reaction solution was diluted with ethyl acetate (4 ml) and diisopropyl ether (4 ml), after which water (4 ml) and 1N HCl(0.25 ml) were added to the diluted solution. The resulting mixture was stirred well. Crystals thus formed were recovered from said mixture by filtration, washed with water and with a mixture of ethyl acetate and diisopropyl ether(1 : 1 by volume), successively and dried to afford 88 mg (yield 70%) of a product. This product was found to be the same as the product of Example 1, that is, p-nitrobenzyl 7-phenylacetamido-3-methylthio-3-cephem-4-carboxylate.

EXAMPLE 3

The reaction and after-treatment procedures of Example 2 were repeated except that piperidine (0.99 ml) was used as the secondary amine in place of pyrrolidine, and there were obtained pale yellow crystals (89 mg; 71%). This product was the same as the product of Example 1.

EXAMPLE 7

The reaction and after-treatment procedures of Example 2 were repeated except that diethylamine (1.04 ml) was used as the secondary amine in place of pyrrolidine, and there were yielded pale yellow crystals (83 mg; 66%). This product was the same as the product of Example 1.

EXAMPLE 5

Diphenylmethyl 7-phenylacetamido-3-acetylthio-3-cephem-4-carboxylate (140 mg) was dissolved in N,N-dimethylformamide (1.5 ml) and the resulting solution was cooled to 5° C. To the cooled solution was slowly added a 0.25 ml-portion of such a mixture of triethylamine (1.39 ml) as the tertiary amine and morpholine (0.84 ml) as the secondary amine which had been diluted in benzene as diluent to give 10 ml of said mixture. The resulting reaction mixture was stirred at that temperature for 10 minutes, to produce the triethylamine salt of diphenylmethyl 7-phenylacetamido-3-mercapto-3-cephem-4-carboxylate in the resulting reaction solution. Dimethyl sulfate (48 μl) was added as methylating agent to the said reaction solution and the mixture was stirred for further 10 minutes to proceed with the reaction. To the reaction solution thus obtained were added ethyl acetate (8 ml) and water (8 ml), and the resultant mixture was stirred well before the organic layer being separated.

The organic lyer so separated was washed with water and an aqueous sodium chloride solution, successively, dried over magnesium sulfate and concentrated under a reduced pressure to afford a pale yellow oil. This oil was purified by a column chromatography using silica gel (15 g) to give diphenylmethyl 7-phenylacetamido-3-methylthio-3-cephem-4-carboxylate as colourless crystals (80 mg; 60%).

NMR(CDCl$_3$):
2.08 (3H, s),
3.12, 3.38(2H, ABq, J=17Hz),
3.64 (2H, s),
4.94 (1H, d, J=4.5Hz),
5.61 (1H, dd, J=4.5Hz, 9Hz),
6.70 (1H, d, J=9Hz),
6.86 (1H, s),
7.20–7.40 (15H, m)

EXAMPLE 6

The reaction and purification procedures of Example 5 were repeated except that diphenylmethyl 7-phenylacetamido-3-acetylthio-2-cephem-4-carboxylate (140 mg) was used in place of diphenylmethyl 7-phenylacetamido-3-acetylthio-3-cephem -4-carboxylate. There was obtained diphenylmethyl 7-phenylacetamido-3-methylthio-3-cephem-4-carboxylate (75 mg; 56%) as the desired product. This product was the same as the product of Example 5 and was free from the Δ² isomer when analyzed by NMR analysis.

EXAMPLE 7

To a solution of diphenylmethyl 7-phenylacetamido-3-benzoylthio-3-cephem-4-carboxylate (156 mg) in N,N-dimethylformamide (1.5 ml) was slowly added, under ice-cooling, a 0.25 ml-portion of such a mixture of triethylamine (1.39 ml) and morpholine (0.84 ml) which had been diluted in benzene as diluent to give 10 ml of said mixture. The resulting reaction mixture was stirred at that temperature for 30 minutes, to form triethylamine salt of diphenylmethyl 7-phenylacetamido-3-mercapt-3-cephem-4-carboxylate in the reaction solution as obtained. Thin layer chromatography was used to confirm the disappearance of the starting material on a sample or samples taken out from the resulting reaction solution. Then, dimethyl sulfate (36 μl) was added to the said reaction solution and the reaction was effected under ice-cooling for further 10 minutes. After-treatment and purification were carried out in the same manner as in Example 5, affording diphenylmethyl 7-phenylacetamido-3-methylthio-3-cephem-4-carboxylate (98 mg; 73%) as colourless crystals.

EXAMPLE 8

The reaction and purification procedures of Example 7 were repeated except that diphenylmethyl 7-phenylacetamido-3-(4-methoxybenzoylthio)-3-cephem-4-carboxylate (163 mg) was used in place of diphenylmetyl 7-phenylacetamido-3-benzoylthio-3-cephem-4-carboxylate. Diphenylmethyl 7-phenylacetamido-3-methylthio-3-cephem-4-carboxylate (105 mg; 79%) was obtained as colourless crystals.

EXAMPLE 9

Diphenylmethyl 7-phenylacetamido-3-acetylthio-3-cephem-4-carboxylate (1.68 g) was dissolved in hexamethylphosphoric triamide (18 ml) and the resulting solution was cooled to 5° C. To the cooled solution was added a 3.0 ml-portion of such a solution of triethylamine (1.39 ml) and morpholine (0.84 ml) which had been diluted in benzene as diluent to totally 10 ml. The resulting reaction mixture was stirred at that temperature for 15 minutes. Then, tetrahydrofurfuryl bromide (2.48 g) was added to the resulting reaciion solution, and the mixture so obtained was stirred at room temperature for further 2 hours to proceed with the reaction. The resulting reaction solution was diluted with ethyl acetate (40 ml) and the diluted solution was washed with cold water two times and then with an aqueous sodium chloride solution and dried over magnesium sulfate. The dried solution was subjected to distillation at a reduced pressure to remove the solvent, and the resulting yellow oil was purified by a column chromatography on silica gel (150 g), affording diphenylmethyl 7-phenylacetamido-3-tetraphydrofurfurylthio-3-cephem-4-carboxylate (360 mg; 20%) as a colourless powder.

NMR(CDCl₃):
1.40–2.10(4H, m),
2.65 (2H, m),
3.30 (2H, m),
3.57 (2H, s),
3.50–4.00(5H, m),
4.88 (1H, d, J=4Hz),
5.60 (1H, dd, J=4Hz, 8Hz),
6.68 (1H, d, J=8Hz),
6.85 (1H, s),
7.20–7.50(15H, m)

EXAMPLE 10

Diphenylmethyl 7-phenylacetamido-3-acetylthio-3-cephem-4-carboxylate (280 mg) was dissolved in dichloromethane (4 ml) and the solution was ice-cooled. To the cooled solution was added under ice-cooling a 1.0 ml-portion of such a solution of trietylamine (0.70 ml) and morpholine (0.44 ml) which had been diluted in dichloromethane as diluent to totally 10 ml. The resulting reaction mixture was stirred at that temperature for the reaction. During this, compound of formula (9) was formed in the resulting reaction solution according to the following reaction equation.

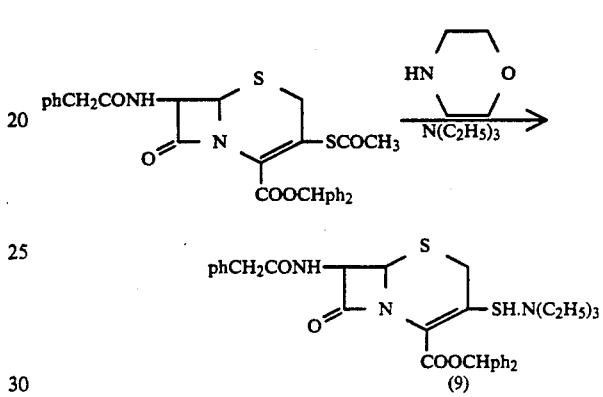

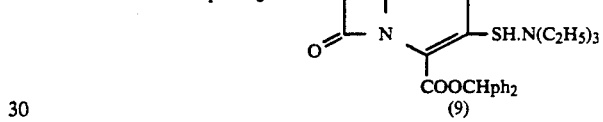

wherein ph means phenyl group and has the same meaning hereinafter.

On the other hand, 5-hydroxymethyl-4-methylthiazole (78 mg) and 2-fluoro-1-methylpyridinium p-toluenesulfonate (170 mg) were dissolved in dichloromethane (2 ml). Triethylamine (84 μl) was added to the resulting solution. The mixture so obtained was stirred at room temperature for 30 minutes to effect the intended reaction. During this reaction, the compound of formula (10) was formed in the resulting reaction solution according to the following equation.

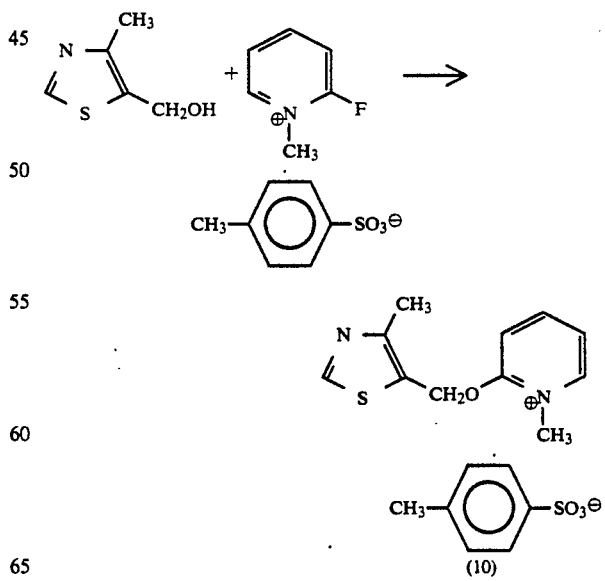

This reaction solution was added to the first-mentioned reaction solution containing the compound of formula (9) under ice-cooling and the resultant mixture was stirred at that temperature for further 10 minutes. The resulting reaction solution was washed successively with cold water, a dilute hydrochloric acid and an aqueous sodium chloride solution and then dried over magnesium sulfate. The solvent was distilled off under a reduced pressure and the residue was purified by column chromatography on silica gel (20 g) to afford diphenylmethyl 7-phenylacetamido-3-[(4-methylthiazol-5-yl)methylthio]-3-cephem-4-carboxylate (200 mg; 63%) as colourless crystals.

This compound has formula (11):

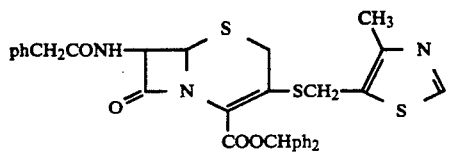

NMR(DMSO-$d_6$):
2.30 (3H, s),
3.50 (2H, s),
3.81 (2H, s),
4.34 (2H, s),
5.09 (1H, d, J=4Hz),
5.65 (1H, dd, J=4Hz, 9Hz),
6.82 (1H, s),
7.20–7.50(15H, m),
8.81 (1H, s),
9.06 (1H, d, J=9Hz)

EXAMPLE 11

Diphenylmethyl 7-phenylacetamido-3-acetylthio-3-cephem-4-carboxylate (560 mg) was dissolved in dichloromethane (6 ml). To the resulting solution was added, under ice-cooling, a 2.0 ml-portion of such a solution of triethylamine (0.70 ml) and morpholine (0.44 ml) which had been diluted in dichloromethane to totally 10 ml. The resulting mixture was stirred at that temperature for 15 minutes to conduct the reaction, whereby forming triethylamine salt of diphenylmethyl 7-phenylacetamido-3-mercapt-3-cephem-4-carboxylate in the resulting reaction solution. Then, α-bromo-γ-butyrolactone (215 mg) was added to said resulting reaction solution and the mixture so obtained was stirred for further 2 hours to effect the reaction. The resulting reaction solution was washed with water, dried over magnesium sulfate and concentrated under a reduced pressure to give a brown solid mass. This solid mass was purified by column chromatography on silica gel (40 g) and crystallized from ethyl acetate-diisopropylether to afford diphenylmethyl 7-phenylacetamido-3-(2-oxotetrahydrofuran-3-ylthio)-3-cephem-4-carboxylate (440 mg; 73%) as pale yellow crystals. Thin layer chromatography of this product showed two spots and NMR analysis showed that the product was a mixture (1:1) of diastereomers in respect of the 2-oxotetrahydrofuran-3-yl group in the side chain at the 3-position of the cephem ring.

NMR(CDCl$_3$):
1.73–2.20(1H, m),
2.20–2.70(1H, m),
3.35–3.75(3H, m),
3.60 (2H, s),
4.15 (1H, t, J=8Hz),
4.17 (1H, t, J=8Hz),
4.95 (0.5H, d, J=4Hz),
4.96 (0.5H, d, J=4Hz),
5.75 (1H, dd, J=4Hz, 9Hz),
6.30 (1H, d, J=9Hz),
6.84 (0.5H, s),
6.92 (0.5H, s),
7.20–7.40(15H, m)

EXAMPLE 12

Diphenylmethyl 7-phenylacetamido-3-acetylthio-3-cephem-4-carboxylate (1.68 g) was dissolved in hexamethylphosphoric triamide (18 ml) and the solution was cooled to 5° C. To the cooled solution was added a 3.0 ml-portion of such a solution (10 ml) of triethylamine (1.39 ml) and morpholine (0.84 ml) as diluted with benzene. The resulting mixture was stirred at that temperature for minutes to proceed with the reaction. Then, 3-bromotetrahydrofuran (2.27 g) was added to the resulting reaction solution and the stirring was continued at room temperature for 2 hours to effect the reaction.

The reaction solution thus obtained was diluted with ethyl acetate (30 ml) and cold water (30 ml) to separate the organic layer. The organic layer separated was washed with cold water and with an aqueous sodium chloride solution, in order, and dried over magnesium sulfate. The solvent used was distilled off to give a yellow oil as the residue. This oil was purified by column chromatography on silica gel (65 g), affording diphenylmethyl 7-phenylacetamido-3-(tetrahydrofuran-3-ylthio)-3-cephem-4-carboxylate (600 mg; 34%) as colourless crystals.

NMR(DMSO-$d_6$):
1.4–1.8 (1H, m),
1.9–2.3 (1H, m),
3.2–4.0 (7H, m),
3.50 (2H, s),
5.12 (1H, d, J=4Hz),
5.61 (1H, dd, J=4Hz, 9Hz),
6.82 (1H, s),
7.10–7.50(15H, m),
9.05 (1H, d, J=9Hz)

EXAMPLE 13

Diphenylmethyl 7-[(Z)-2-(2-tritylaminothiazol-4-yl)-2-(2-t-butoxycarbonyl-2-propoxyimino)acetamido]-3-acetylthio-3-cephem-4-carboxylate (350 mg) was dissolved in dichloromethane (4 ml) and the solution was cooled to 5° C. To the cooled solution was added a 0.77 ml-portion of such a solution (25 ml) of triethylamine (1.74 ml) and morpholine (1.09 ml) as diluted with dichloromethane. The resulting mixture was stirred at that temperature for 15 minutes to conduct the reaction. In the reaction solution was formed a compound of formula (12)

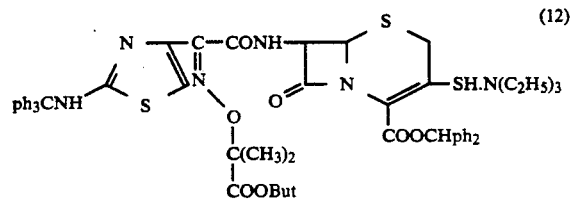

wherein ph represents phenyl group and But represents t-butyl group. On the other hand, 1-diphenylmethyloxy-2-hydroxymethyl-5-(4-methoxybenzyloxy)4- pyridone (205 mg) and 2-fluoro-1-methylpyridinium p-toluenesulfonate (131 mg) were suspended in dichloromethane (2 ml). To the suspension obtained was added triethylamine (65 μl), and the resultant mixture was stirred at room temperature for 30 minutes to conduct the reaction. During this reaction, the compound of formula (13) was formed in the resulting reaction solution according to the following equation.

thylthio]-3-cephem-4-carboxylate (320 mg; 59%) as pale yellow powder. This compound has formula (14):

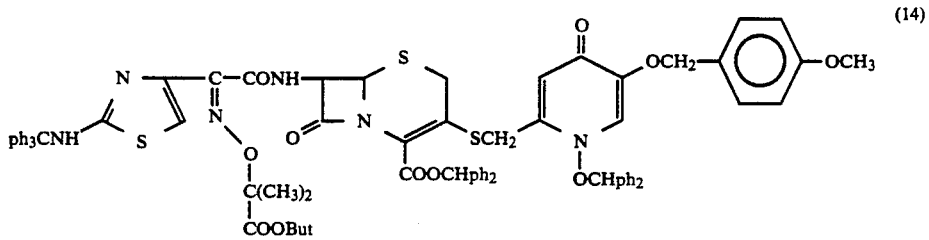

(14)

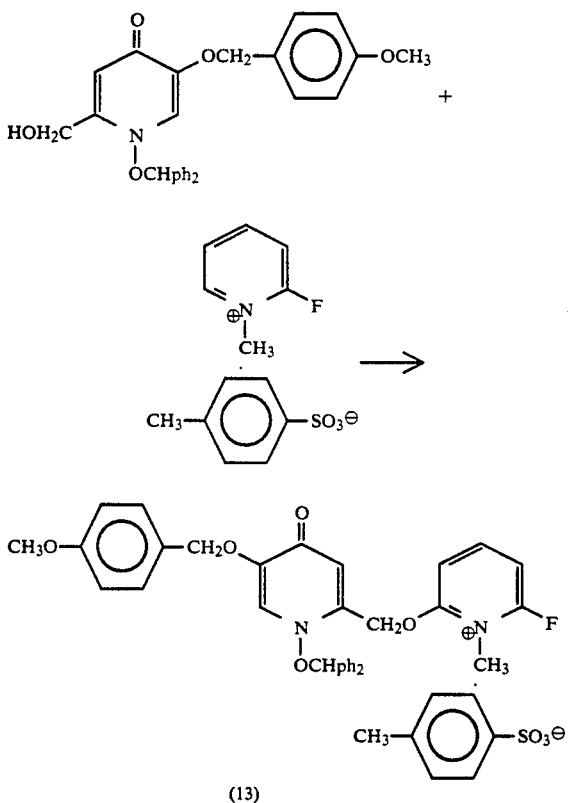

(13)

This reaction solution containing the compound of formula (13) was added to the first-mentioned reaction solution containing the compound of formula (12) under ice-cooling, and the mixture obtained was stirred for further 30 minutes to effect the reaction. The resulting reaction solution was diluted with dichloromethane (10 ml), then washed successively with cold water and with an aqueous sodium chloride solution and dried over magnesium sulfate. The solvent used was distilled off to leave a yellow oil which was then purified by column chromatography on silica gel (65 g), yielding diphenylmethyl 7-[(Z)-2-(2-tritylaminothiazol-4-yl)-2-(2-t-butoxycarbonyl-2-propoxyimino)acetamido]-3-[1-diphenyl-methyloxy-5-(4-methoxybenzyloxy)-4-pyridone-2ylme- NMR(CDCl₃):
1.37 (9H, s),
1.56 (3H, s),
1.61 (3H, s),
3.10, 3.14(2H, ABq, J=18Hz),
3.37 (2H, s),
3.73 (3H, s),
4.72 (2H, s),
4.83 (1H, d, J=5Hz),
5.85 (1H, s),
5.86 (1H, dd, J=5Hz, 9Hz),
6.10 (1H, s),
6.63–7.40(40H, m),
8.12 (1H, d, J=9Hz)

EXAMPLE 14

Diphenylmethyl 7-[(Z)-2-(2-tritylaminothiazol-4-yl)2-(2-t-butoxycarbonyl-2-propoxyimino)acetamido]-3-acetylthio-3-cephem-4-carboxylate (200 mg) was dissolved in dimethylformamide (2 ml) and the solution was cooled to 5° C. To the cooled solution was added a 0.4 ml-portion of such a solution (10 ml) of triethylamine (0.7 ml) and morpholine (0.44 ml) as diluted with benzene. The resulting mixture was stirred at that temperature for 15 minutes to conduct the reaction, affording triethylamine salt of diphenylmethyl 7-[(Z)-2-(2-tritylaminothiazol-4-yl)-2-(2-t-butoxycarbonyl-2-propoxyimino)acetamido]-3-mercapto-3-cephem-4-carboxylate in the resulting reaction solution. To this resulting reaction solution was added 1-methyl-2-bromomethyl-5-(4-methoxybenzyloxy)-4-pyridone (102 mg), and the mixture obtained was stirred for further 30 minutes to proceed with the reaction. The reaction solution so obtained was diluted with ethyl acetate (10 ml), then washed successively with cold water and with an aqueous sodium chloride solution and dried over magnesium sulfate. The solvent used was distilled off to leave an oil which was then purified by column chromatography on silica gel (25 g), affording diphenylmethyl 7-[(Z)-2-(2-tritylaminothiazol-4-yl)-2-(2-t-butoxycarbonyl-2-propoxyimino)acetamido]-3-[1-methyl-5-(4-methoxybenzyloxy) pyridin-4-on-2-ylmethylthio]-3-cephem-4-carboxylate (150 mg; 62%) as a colourless powder.

NMR(CDCl₃):
1.37 (9H, s),
1.55 (3H, s),
1.60 (3H, s),
3.23 (3H, s),
3.31, 3.44(2H, ABq, J=8Hz),
3.51 (2H, s),
3.73 (3H, s),
5.00 (1H, d, J=5Hz),
5.05 (2H, s), 5.94 (1H, dd, J=5Hz, 9Hz),
6.20 (1H, s),
6.68–7.40 (30H, m),
8.22 (1H, d, J=9Hz)

EXAMPLE 15

Diphenylmethyl 7-[(Z)-2-(2-tritylaminothiazol-4-yl)-2-methoxyiminoacetamido]-3-acetylthio-3-cephem-4-carboxylate (390 mg) was dissolved in dichloromethane (4 ml) and the solution was cooled to 5° C. To the cooled solution was added a 1.0 ml-portion of such a solution (25 ml) of triethylamine (1.74 ml) and morpholine (1.09 ml) as diluted with dichloromethane. The resulting mixture was stirred at that temperature for 15 minutes to conduct the reaction, affording the reaction solution.

On the other hand, 1-diphenylmethyloxy-2-hydroxymethyl-5-(4-methoxybenzyloxy)-4-pyridone (365 mg) and 2-fluoro-1-methylpyridinium.p-toluenesulfonate (170 mg) were suspended in dichloromethane (4 ml). Triethylamine (84 μl) was added to the resulting suspension and the mixture so obtained was stirred at room temperature for 30 minutes to effect the reaction. Thus, the formation of the compound of formula (13) as shown in Example 13 was obtained in the resulting reaction solution. This reaction solution was added to the first-mentioned reaction solution under ice-cooling, and the resulting mixture was stirred for further 30 minutes. The reaction solution so obtained was diluted with dichloromethane (15 ml), then washed successively with cold water and with an aqueous sodium chloride solution and dried over magnesium sulfate. The solvent used was distilled off and the residue was purified by column chromatography on silica gel (65 g), to afford diphenylmethyl 7-[(Z)-2-(2-tritylaminothiazol-4yl)-2-methoxyiminoacetamido]-3-]1-diphenylmethyloxy-5-(4-methoxybenzyloxy)-4-pyridon-2-ylmethylthio]-3-cephem-4-carboxylate (250 mg; 39%) as pale yellow powder.

NMR(CDCl₃):
3.10, 3.20(2H, ABq, J=18Hz),
3.37, 3.41(2H, ABq, J=18Hz),
3.72 (3H, s),
4.70 (2H, s),
4.88 (1H, d, J=5Hz),
5.83 (1H, dd, J=5Hz, 8Hz),
5.86 (1H, s),
6.06 (1H, s),
6.63–7.40 (41H, m)

Compounds of formula (1) which are used as the starting compound in the process of this invention may be prepared by reacting a compound of formula (A)

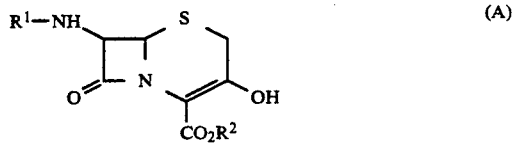

wherein R¹ and R² have the meanings defined above for the compound of formula (1), with diphenyl chlorophosphate in an anhydrous organic solvent in the presence of a base such as a trialkylamine, whereby to form a cephem-enolphosphate compound of formula (B)

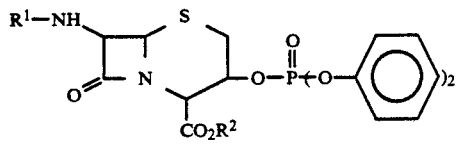

and then reacting the compound of formula (B) with a thio acid of formula (C)

R³COSH      (C)

wherein R³ have the meaning defined above for the compound of formula (1), preferably thioacetic acid or thiobenzoic acid in an organic solvent in the presence of a base such as a trialkylamine.

The preparation of the starting compound used in Example 1 is illustrated by Reference Example 1 given below.

REFERENCE EXAMPLE 1 p-Nitrobenzyl 7-phenylacetamido-3-hydroxy-3-cephem-4-carboxylate (14.1 g) was suspended in acetonitrile (140 ml) and the resulting suspension was cooled to −10° C. To the cooled suspension were slowly added N,N-diisopropylethylamine (6.3 ml) and diphenyl chlorophosphate (9.7 g), and the mixture obtained was stirred at 0° C. for 90 minutes to conduct the reaction. By this reaction, there was formed the compound of formula (15) (in the form of a mixture of the Δ² isomer and Δ³ isomer) in the resulting reaction solution according to the following equation.

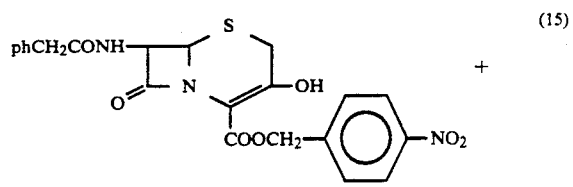

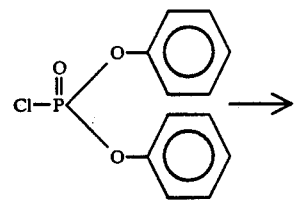

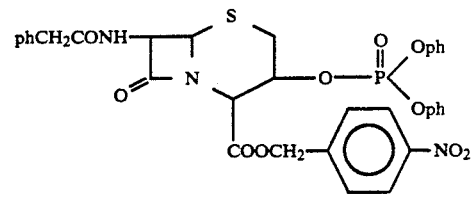

wherein ph represents phenyl group.

On the other hand, thioacetic acid (4.4 ml) was dissolved in acetonitrile (50 ml), to which was then added dropwise N,N-diisopropylethylamine (10.5 ml), while maintaining the temperature below −20° C., so that a solution was prepared. This solution was added to the first-mentioned reaction solution containing the cephem-enolphosphate of formula (15), followed by adding, N,N-diisopropylethylamine (6.3 ml) and stirring the resulting reaction mixture at a temperature of −15° C. ~ −10° C. for 90 minutes to effect the reaction. Thus, there was produced the compound of formula (16):

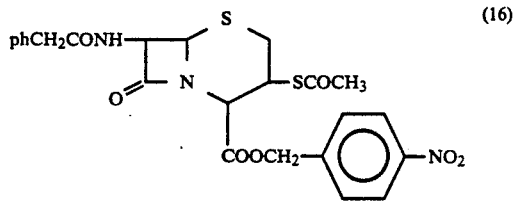

The reaction solution containing the compound of formula (16) was added to a mixture of cold water (200 ml), 2N HCl (50 ml) and ethyl acetate (300 ml), and the resulting mixture was well stirred before the organic layer being separated. The organic layer so separated was washed successively with water and with an aqueous sodium chloride solution and dried over magnesium sulfate. The solvent used was distiled off to leave a red oil. This oil was purified by column chromatography on silica gel (500 g), to afford the $\Delta^3$ isomer of the compound of formula (16), i.e. p-nitrobenzyl 7-phenylacetamido-3-acetylthio-3-cephem-4-carboxylate (13.6 g; 64%) as pale brown crystals.

NMR(CDCl₃):
2.29 (3H, s),
3.30, 3.84 (2H, ABq, J=18Hz),
3.60 (2H, s),
5.02 (1H, d, J=4Hz),
5.27 (2H, s),
5.83 (1H, dd, J=4Hz, 9Hz),
6.10 (1H, d, J=9Hz),
7.20–7.30 (5H, m),
7.48 (2H, d, J=9Hz),
8.15 (2H, d, J=9Hz)

Reference Example 2 given below illustrates the preparation of the starting compound used in Example 7.

REFERENCE EXAMPLE 2

Diphenylmethyl 7-phenylacetamido-3-diphenylphosphoryloxy-cephem-4-carboxylate (as a mixture of the $\Delta^2$ isomer and $\Delta^3$ isomer) (370 mg) was dissolved in N,N-dimethylformamide (4 ml) and the solution was cooled to −20° C. To the cooled solution were added thiobenzoic acid (0.12 ml) and N,N-diisopropylethylamine (0.18 ml), and the reaction was conducted under ice-cooling for 3 hours. The resulting reaction solution was diluted with ethyl acetate and then washed successively with water, a dilute hydrochloric acid and a dilute aqueous sodium hydrogen carbonate and dried over magnesium sulfate. The solvent used was distilled off to leave a pale yellow oil. The oil was purified by column chromatography on silica gel (35 g) and then crystallized from ethyl acetate-diisopropylether to afford diphenylmethyl 7-phenylacetamido-3-benzoylthio-3-cephem-4-carboxylate (190 mg; 61%) as colourless crystals.

NMR(CDCl₃):
3.39, 3.87 (2H, ABq, J=18Hz),
3.63 (2H, s),
5.19 (1H, d, J=4Hz),
5.85 (1H, dd, J=4Hz, 9Hz),
6.05 (1H, d, J=9Hz),
6.94 (1H, s), 7.00–7.70 (20H, m)

INDUSTRIAL UTILITY OF THE INVENTION

As explained above, this invention provides a process by which esters of a 7-acylamido-3-substituted-thio-3-cephem-4-carboxylic acid can be prepared preferentially, conveniently and efficiently by using 7-acylamido-3-acylthio-3-or -2-cephem-4-carboxylic acid esters or a mixture of these 3-cephem compond and 2-cephem compound as the starting compound.

We claim:

1. A process for the preparation of a 3-substituted thio-3-cephem compound of structure (5)

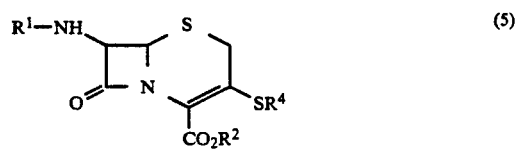

wherein $R^1$ is an acyl group; $R^2$ is a carboxyl-protecting group; and $R^4$ is a lower alkyl group, a cycloalkyl group or a heterocyclic group or a heterocyclic group-substituted methyl group, which comprises the steps of reacting a 3-acylthio-cephem compound of structure (1)

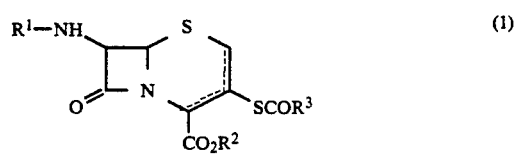

wherein $R^1$ and $R^2$ each have the meaning as defined above; $R^3$ is a lower alkyl group containing up to 6 carbon atoms, an aryl group or a substituted aryl group, said alkyl or aryl group being such that the acyl group —COR³ containing said alkyl or aryl group as $R^3$ is reactable with tertiary amine (2) and secondary amine as defined below; and the dotted line given in the formula (1) represents that the compound of formula (1) is either a compound having a $\Delta^2$ double bond present in the 6-membered ring or a compound having a $\Delta^3$ double bond present in the 6-membered ring or a mixture of the compounds of these two types, with a tertiary amine of structure (2)

wherein $R^5$, $R^6$ and $R^7$ are the same or different and individually represents lower alkyl group; or $R^5$ is a lower alkyl group and $R^6$ and $R^7$ taken together with a nitrogen atom to which $R^6$ and $R^7$ are attached form a nitrogen-containing heterocyclic ring having or not having an oxygen atom as a hetero atom, and also with a secondary amine to give a compound of structure (3)

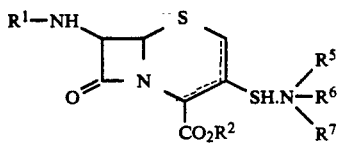
(3)

wherein $R^1$, $R^2$, $R^5$, $R^6$ and $R^7$ each having the meanings as defined above; and the dotted line given in the formula (3) also has the meaning as defined above; and then reacting the compound of structure (3) thus formed with a compound of structure (4)

$$R^4-X \qquad (4)$$

wherein $R^4$ has the meaning as defined above; and X is selected from the group consisting of halogen, methanesulfonyloxy, p-toluenesulfonyloxy, trifluoromethanesulfonlyloxy and alkoxysulfonyloxy, to form the 3-substituted thio-3-cephem compound of structure (5) above.

2. A process according to claim 1 wherein the tertiary amine of formula (2) is a tri-(lower)alkylamine, preferably triethylamine.

3. A process according to claim 1 wherein the secondary amine used is morpholine, pyrrolidine, piperidine, piperazine or diethylamine.

4. A process according to claim 1 wherein a compound of formula (1) is reacted with 1.0–1.1 molar equivalents of a tertiary amine of formula (2) and with 1.0–1.1 molar equivalents of a secondary amine per 1 molar equivalent of the compound of formula (1) in an organic solvent at room temperature or under ice-cooling, and the resulting compound of formula (3) is then reacted with 1.0–5.0 molar equivalents of a compound of formula (4) per 1 molar equivalent of the compound of formula (3) in an organic solvent at room temperature or under ice-cooling.

* * * * *